United States Patent
Su

(10) Patent No.: US 11,414,548 B2
(45) Date of Patent: Aug. 16, 2022

(54) ENHANCED RADIATION SHIELDING WITH CONFORMAL, LIGHTWEIGHT NANOPARTICLE-POLYMER COMPOSITE

(71) Applicant: Northeastern University, Boston, MA (US)

(72) Inventor: Ming Su, Newton, MA (US)

(73) Assignee: Northeastern University, Boston, MA (US)

( * ) Notice: Subject to any disclaimer, the term of this patent is extended or adjusted under 35 U.S.C. 154(b) by 1 day.

(21) Appl. No.: 16/749,400

(22) Filed: Jan. 22, 2020

(65) Prior Publication Data

US 2020/0231811 A1 Jul. 23, 2020

Related U.S. Application Data

(60) Provisional application No. 62/795,185, filed on Jan. 22, 2019.

(51) Int. Cl.
| | |
|---|---|
| *C08L 83/04* | (2006.01) |
| *C08L 1/00* | (2006.01) |
| *C08K 3/08* | (2006.01) |
| *C08J 5/18* | (2006.01) |
| *A61B 6/10* | (2006.01) |
| *G21F 1/10* | (2006.01) |

(52) U.S. Cl.
CPC .............. *C08L 83/04* (2013.01); *A61B 6/107* (2013.01); *C08J 5/18* (2013.01); *C08K 3/08* (2013.01); *C08L 1/00* (2013.01); *G21F 1/10* (2013.01); *C08J 2301/02* (2013.01); *C08J 2383/04* (2013.01); *C08K 2003/0837* (2013.01); *C08K 2201/005* (2013.01); *C08L 2201/08* (2013.01); *C08L 2203/16* (2013.01)

(58) Field of Classification Search
CPC .............. C08K 3/08; C08K 2003/0837; C08K 2003/0887; C08K 9/04; C08L 1/00; C08L 83/04

See application file for complete search history.

(56) References Cited

U.S. PATENT DOCUMENTS

| | | | |
|---|---|---|---|
| 9,045,674 B2 * | 6/2015 | Iruvanti | ................ B82Y 30/00 |
| 10,294,383 B2 * | 5/2019 | Shoseyov | ................ C08J 7/048 |
| 2017/0152411 A1 * | 6/2017 | Mihara | ................ H01L 21/78 |

FOREIGN PATENT DOCUMENTS

CN 108034148 A * 5/2018

OTHER PUBLICATIONS

Machine translation of CN 108034148 A, published May 15, 2018. (Year: 2018).*

(Continued)

*Primary Examiner* — Vickey Nerangis
(74) *Attorney, Agent, or Firm* — Dana M. Gordon; Foley Hoag LLP

(57) ABSTRACT

Disclosed is a composite material, comprising a polymer, a plurality of metal nanoparticles, and a surface-modifying agent (e.g., nanocellulose). Also disclosed is a method for shielding a subject from electromagnetic radiation, comprising placing one or more composite materials between the subject and a source of electromagnetic radiation, thereby reducing a dose of electromagnetic radiation received by the subject.

15 Claims, 5 Drawing Sheets

(56) References Cited

OTHER PUBLICATIONS

Ambika et al., "Role of Bismuth Oxide as a Reinforcer on Gamma Shielding Ability of Unsaturated Polyester Based Polymer Composites," Journal of Applied Polymer Science, 134:1-7 (2016).
Badawy et al., "Synthesis and Characterizations of Magnetite Nanocomposite Films for Radiation Shielding," Polymer Composites, 38:974-980 (2015).
Christodoulou et al., "Evaluation of the Transmitted Exposure through Lead Equivalent Aprons Used in a Radiology Department, Including the Contribution from Backscatter," Medical Physics, 30(6):1033-1038 (2003).
Curtis, "Limitations on Space Flight Due to Cosmic Radiations," Science, 133:312-316 (1961).
Guo et al., "X-Ray Attenuation Property of Dendrimer-Entrapped Gold Nanoparticles," The Journal of Physical Chemistry C, 114:50-56 (2010).
Gupta et al., "$MnO_2$ Decorated Graphene Nanoribbons with Superior Permittivity and Excellent Microwave Shielding Properties," Journal of Materials Chemistry A, 2:4256-4263 (2014).
Hull, "Radiation Protection," Science, 174:1280-1281 (1971).
Hyun et al., "Efficiency of Lead Aprons in Blocking Radiation—How Protective Are They?" Heliyon, 2:1-14 (2016).
Kandanapitiye et al., "Synthesis, Characterization, and X-Ray Attenuation Properties of Ultrasmall BiOI Nanoparticles: Toward Renal Clearable Particulate Ct Contrast Agents," Inorganic Chemistry, 53:10189-10194 (2014).
Kazempour et al., "Assessment of the Radiation Attenuation Properties of Several Lead Free Composites by Monte Carlo Simulation," Journal of Biomedical Physics & Engineering, 5(2):67-76 (2015).
Kim et al., "Enhanced X-Ray Shielding Ability of Polymer-Nonleaded Metal Composites by Multilayer Structuring," Industrial & Engineering Chemistry Research, 54:5968-5973 (2015).
Kim et al., "HDPE Surface Functionalization by Low-Energy Ion-Beam Irradiation under a Reactive $O_2$ Environment and Its Effect on the HDPE/Nylon 66 Blend," Macromolecules, 34:2546-2558 (2001).
Kim et al., "Physical Analysis of the Shielding Capacity for a Lightweight Apron Designed for Shielding Low Intensity Scattering X-Rays," Scientific Reports, 6:27721 (2016).
Li et al., "Effect of Particle Size on Gamma Radiation Shielding Property of Gadolinium Oxide Dispersed Epoxy Resin Matrix Composite," Materials Research Express, 4:035035-035045 (2017).
Li et al., "Gamma Ray Shielding Property, Shielding Mechanism and Predicting Model of Continuous Basalt Fiber Reinforced Polymer Matrix Composite Containing Functional Filler," Materials & Design, 124:121-130 (2017).
Li et al., "PDMS/Single-Walled Carbon Nanotube Composite for Proton Radiation Shielding in Space Applications," Materials Letters, 108:79-83 (2013).
Li et al., "PMMA/MWCNT Nanocomposite for Proton Radiation Shielding Applications," Nanotechnology, 27:234001-234010 (2016).
Liu et al., "Elevated Gamma-Rays Shielding Property in Lead-Free Bismuth Tungstate by Nanofabricating Structures," Journal of Physics and Chemistry of Solids, 112:185-189 (2018).
Martinez et al., "Space Radiation Analysis: Radiation Effects and Particle Interaction Outside the Earth's Magnetosphere Using GRAS and GEANT4," Acta Astronautica, 72:156-164 (2012).
McCaffrey et al., "Radiation Attenuation by Lead and Nonlead Materials Used in Radiation Shielding Garments," Medical Physics, 34(2):530-537 (2007).
Mesbahi et al., "Shielding Properties of the Ordinary Concrete Loaded with Micro- and Nano-Particles against Neutron and Gamma Radiations," Applied Radiation and Isotopes, 136:27-31 (2018).
Nambiar et al., "Effects of Particle Size on X-Ray Transmission Characteristics of PDMS/Ag Nano- and Microcomposites," 2015 IEEE 15th International Conference on Nanotechnology (IEEE-NANO), 1358-1361 (2015).
Nambiar et al., "Polymer-Composite Materials for Radiation Protection," ACS Applied Materials & Interfaces, 4:5717-5726 (2012).
Reichmanis et al., "Radiation Effects on Polymeric Materials," Irradiation of Polymeric Materials, 527:1-8 (1993).
Roof, "X-Ray Absorption Coefficients of Thorium, Uranium, and Plutonium—Experimental Determination and Theoretical Interpretation," Physical Review, 113(3):820-825 (1959).
Slaba et al., "Optimal Shielding Thickness for Galactic Cosmic Ray Environments," Life Sciences in Space Research, 12:1-15 (2017).
Soylu et al., "Gamma Radiation Shielding Efficiency of a New Lead-Free Composite Material," Journal of Radioanalytical and Nuclear Chemistry, 305:529-534 (2015).
Tishkevich et al., "Effect of the Synthesis Conditions and Microstructure for Highly Effective Electron Shields Production Based on Bi Coatings," ACS Applied Energy Materials, 1:1695-1702 (2018).
Viegas et al., "Increased X-Ray Attenuation Efficiency of Graphene-Based Nanocomposite," Industrial & Engineering Chemistry Research, 56:11782-11790 (2017).
Wu et al., "One-Dimensional Lead Borate Nanowhiskers for the Joint Shielding of Neutron and Gamma Radiation: Controlled Synthesis, Microstructure, and Performance Evaluation," CrystEngComm, 19:7260-7269 (2017).
Yaffe et al., "Composite Materials for X-Ray Protection," Health Physics, 60(5):661-664 (1991).
Zhang et al., "Enhancing the Neutron Shielding Ability of Polyethylene Composites with an Alternating Multi-Layered Structure," Composites Science and Technology, 150:16-23 (2017).
Zhou et al., "Co-Shielding of Neutron and X-Ray with Bismuth Borate Nanoparticles Fabricated via a Facile Sol-Gel Method," Inorganic Chemistry Communications, 77:55-58 (2017).

* cited by examiner

ENHANCED RADIATION SHIELDING WITH CONFORMAL, LIGHTWEIGHT NANOPARTICLE-POLYMER COMPOSITE

RELATED APPLICATIONS

This application claims the benefit of priority to U.S. Provisional Patent Application No. 62/795,185, filed on Jan. 22, 2019.

GOVERNMENT SUPPORT

This invention was made with government support under Grant Number EB016572 awarded by the National Institutes of Health. The government has certain rights in the invention.

BACKGROUND

Efficient shielding of ionizing X-ray and gamma radiation is required in medical, nuclear and space industries. High Z elements, such as lead, tungsten, bismuth, and uranium, are often used to attenuate X-ray radiation. The shielding ability is dependent on the density and mass of the material, leading to heavy shielding materials. There are limited choices in reducing the mass of a given material for X-ray radiation except using graded-Z shielding composed of a laminate of several materials of different atomic numbers. Further, most shielding materials are rigid solids and lack flexibility for conformal protection.

To form conformal protection, a promising way is to shrink the size of effective metals and add them into a polymer matrix. Even though polymer matrices are inferior to metals for radiation shielding, they offer advantages such as flexibility, workability, chemical stability, and low cost. Lead powders are added into fabrics to form shielding aprons and coverings, but the formation of pin holes in polymer-metal composites allow incident photons to penetrate polymer regions, leading to issue of low shielding ability. In order to compensate for pin holes, extra amount of materials has to be used to achieve sufficient protection which makes units heavier than needed.

The challenge of forming conformal lightweight polymer composites is twofold. It is hard to find a process that can incorporate metal powders in polymer sheets with sufficient metal content for effective radiation attenuation and robust enough to avoid structural deterioration, such as tearing and cracking of polymer. Particles densely packed along incoming radiation direction in composites can stop penetrating photons and enhance shielding ability of polymer-metal composites. The key to formation of densely packed structures is narrow size distribution of particles and uniform dispersion of particles in polymer sheets, which can be stacked to form multilayers with desired shielding. Nanoparticles of high-Z elements have been added in polymer to block X-ray radiation, but the nanoparticles tend to form aggregates in polymer, or leach out of polymer and cause toxic effect to human. Most importantly, the classical mass dependent radiation attenuation is prevalent, and there is no experimental proof over the mass benefit of using nanoparticles in polymer composites. From materials aspect, lead is widely used in powder-loaded shielding sheets, but is very toxic, and may leak due to aging, damage, embrittlement, and cracking of polymer. It is therefore imperative to use other non-toxic metals to minimize negative impact.

SUMMARY

One aspect of the invention relates to a new lightweight nanoparticle-composite for enhanced radiation shielding, where ultra-small bismuth nanoparticles added in a polymer can block X-ray radiation several times more efficiently than microparticles at the same nanoparticle-to-polymer mass ratio. The enhancement in radiation shielding is primarily attributed to close packing of nanoparticles normal to incoming X-ray direction, which is enabled by strong affinity of nanoparticles to interstitial space of cellulose nanofibers and even distribution of nanoparticles inside polymer. Given its low cost, light weight, and structure conformability, bismuth nanoparticle-polymer composite will find its use in a wide range of fields related to personal radiation protection.

In some embodiments, the invention relates to a composite material, comprising a polymer, a plurality of metal nanoparticles, and a surface-modifying agent. In some embodiments, the surface-modifying agent is nanocellulose.

In some embodiments, the invention relates to a film comprising a film comprising one or more composite materials.

In some embodiments, the invention relates to a method for shielding a subject from electromagnetic radiation, comprising placing the composite material between the subject and a source of electromagnetic radiation, thereby reducing a dose of electromagnetic radiation received by the subject.

DETAILED DESCRIPTION

Efficient shielding of ionizing X-ray and y radiation is required in medical, nuclear, and space industries. High Z elements, such as lead, tungsten, bismuth, and uranium, are often used to attenuate X-ray radiation, where the shielding ability is dependent on the density and mass of the material, leading to heavy shielding materials. There are limited choices in reducing the mass of a given material for X-ray radiation except using graded-Z shielding composed of a laminate of several materials of different atomic numbers. Most shielding materials are rigid solids and lack flexibility for conformal protection. To form conformal protection, a promising way is to shrink the size of effective metals and add them into a polymer matrix. Even though polymer matrices are inferior to metals for radiation shielding, they offer advantages, such as flexibility, workability, chemical stability, and low cost. Lead powders are added into fabrics to form shielding aprons and coverings, but the formation of pinholes in polymer-metal composites allows incident photons to penetrate polymer regions, leading to issue of low shielding ability. To compensate for pinholes, extra amount of materials has to be used to achieve sufficient protection, which makes units heavier than needed.

The void issue can be solved by using ultra-small nanoparticles packed efficiently, so that voids are minimum, and a small amount of nanoparticles can be used to achieve the same shielding capacity. The polymer-nanoparticle composite can be used to make personal radiation shielding equipment such as facemasks, outfits, gloves, and vests. The potential impact is that this polymer composite can achieve better protection against radiation, and can be made lighter than current lead containing protections. The polymers can include cellulose, polyamide, polyacrylonitrile, polyethylene or polypropylene.

Figure 1:
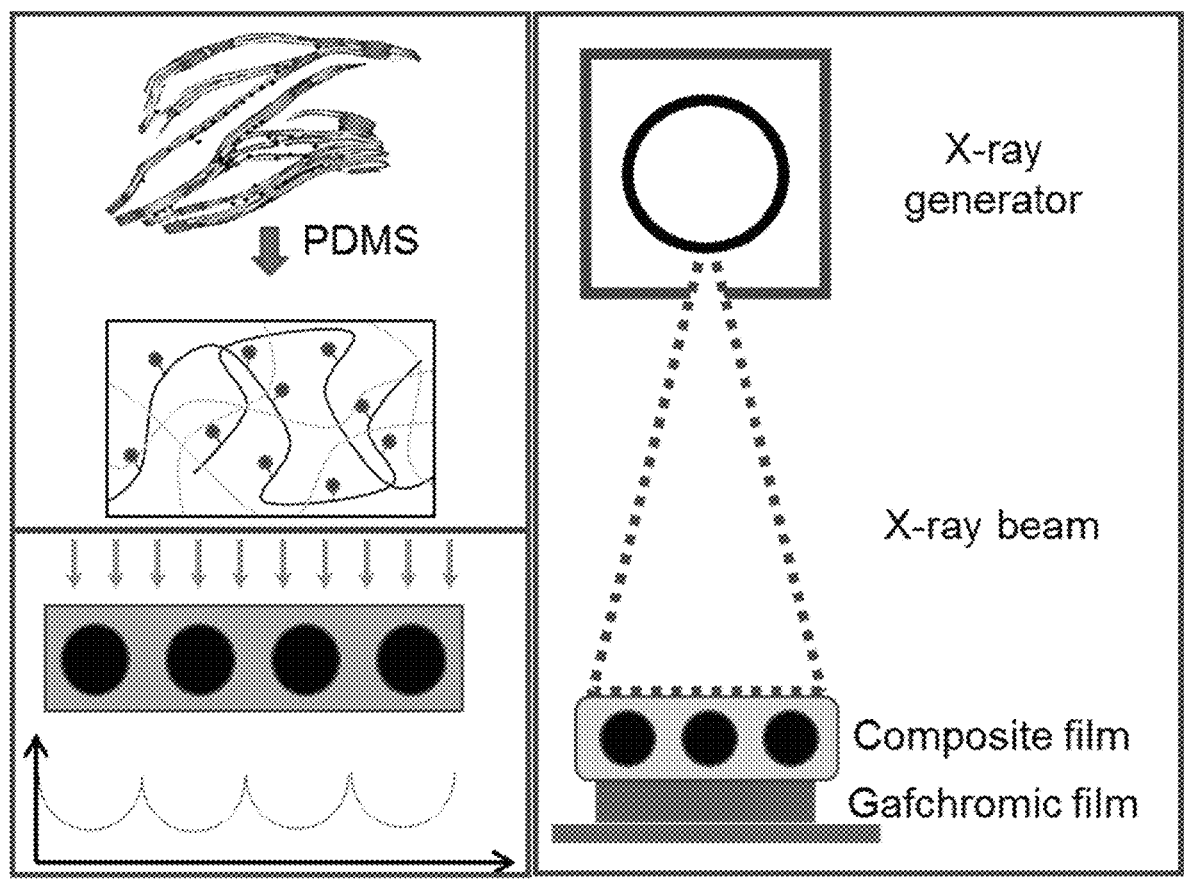
FIG. 1 shows enhanced radiation shielding with polymer-nanoparticle composites, where ultra-small bismuth nanoparticles are prepared using cellulouse nanofibers as templates (left). Scheme of X-ray transmission measurement of polymer-nanoparticle thin film is shown on the right.

In some embodiments, the invention relates to a nanoparticle-polymer composite for enhanced shielding of X-ray radiation, in which bismuth nanoparticles made with cellulose nanofibers form composite with polydimethylsiloxane (PDMS) (FIG. 1). The X-ray radiation shielding abilities of the nanoparticle-polymer composite was assessed in transmission mode and compared to those of microparticle composites. It was found that the nanoparticles can effectively shield X-ray radiation at much lower nanoparticle-to-polymer mass ratio without sacrificing mechanical strength of polymer. A four-fold reduction in the total mass of bismuth material is identified at 2% mass ratio when 5 nm nanoparticles are used in composite to shield a given flux and energy of radiation, compared to when bismuth microparticles are used. The enhanced radiation shielding is attributed to close packing of nanoparticles normal to incoming X-ray direction, which is enabled by strong affinity of nanoparticles to the interstitial space of cellulous nanofibers and even distribution of nanoparticles in polymer matrix. Given its low cost, light weight and structure conformability, bismuth nanoparticle-polymer composite will find its use in a wide range of fields related to personal radiation protection.

Figure 2:
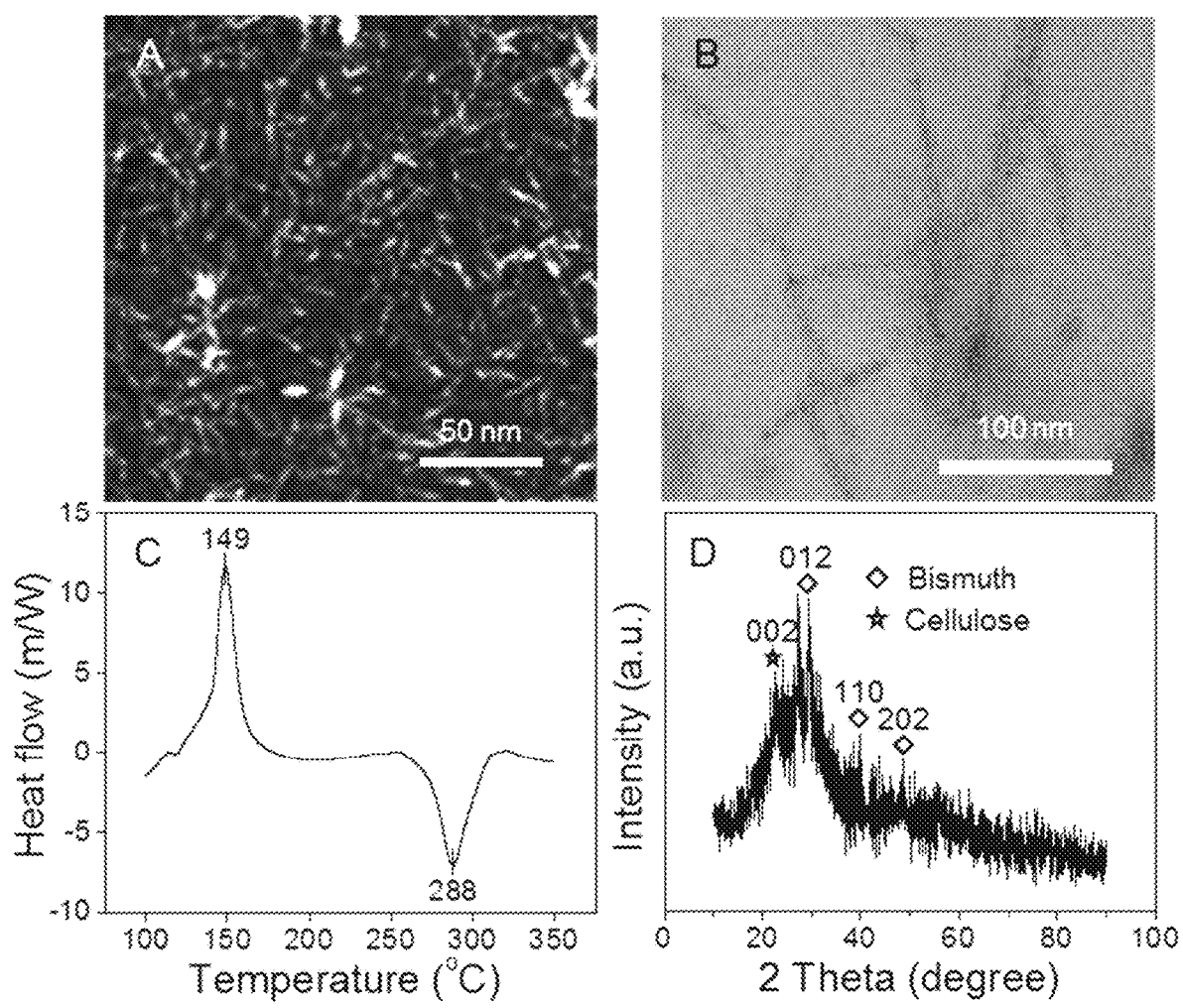
FIG. 2 shows an AFM image of cellulouse nanofibers (A); TEM image (B), DSC curve (C) and XRD spectrum (D) of bismuth nanoparticles decorated around cellulouse nanofibers.

FIG. 2 contains an AFM image of cellulose nanofibers (A), whose average length and diameter are 150-200 nm, and 5 nm, respectively. The nanofibers are composed of bundles of fibers, and there are interstitial spaces among fibers, as shown in the TEM image in (B). Bismuth ions can bind to oxygen moieties at interstitial spaces of cellulose nanofibers, and can be reduced to bismuth metal atoms, which aggregate to nanoparticles with size in 2-10 nm range evenly distributed over cellulose nanofibers. XRD results shown in FIG. 2 confirms the crystalline nature of bismuth nanoparticles (D), where the diffraction rings and pattern were indexed with metallic bismuth. No diffraction peak or ring has been found for the lattice structure of bismuth oxide ($Bi_2O_3$), meaning that the oxidation of bismuth nanoparticles has been prevented by cellulose nanofibers. DSC results of the cellulous nanofiber-protected nanoparticles (C), demonstrate a melting temperature at around 150° C., which is much lower than that of bulk bismuth at 271° C. The melting temperature reduction was induced by size dependent melting temperature of nanoparticles, and was used to confirm that the diameter of bismuth nanoparticles is around 2 nm using following equation:

$$\frac{T}{T_m} = 1 - \frac{4\sigma}{H\rho d} \qquad (1)$$

where T and $T_m$ are melting points of nanoparticles (423 K), and bulk materials (544 K), respectively, H is the latent heat of fusion of bismuth (54 J/g), $\rho$ is the density of bismuth (9.78 g/cm$_3$), d is the size of nanoparticles, and $\sigma$ is the interfacial energy of bismuth (0.0544 J/m$^2$).

Figure 3:
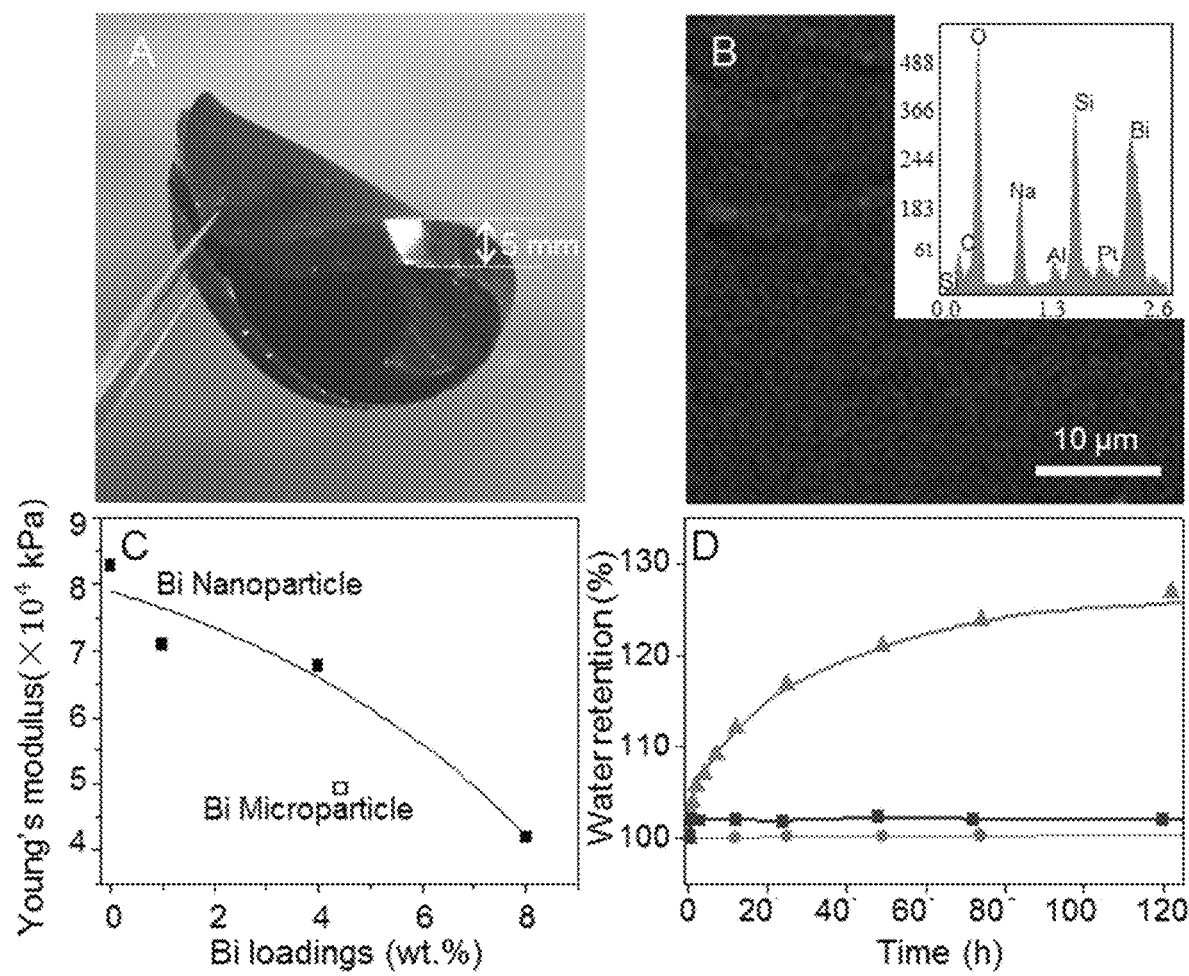
FIG. 3 shows a digital image of a polymer-nanoparticle composite film (8% by mass of nanoparticles) (A); SEM image (B) and EDX spectrum (B inset) of the composite; Young's modulus of polymer-nanoparticle composite at different loading (C), the open square in (C) represents microparticle; water retentions of polymer-particle composites (D), where triangles represent bismuth nanoparticles triangles, squares represent bismuth microparticles, and circles represent PDMS.

Adding bismuth nanoparticles-decorated nanofibers into a polymer matrix provided a composite that maintained the flexibility of the polymer. FIG. 3 shows an optical image of a bended composite film which contains 1% by mass of bismuth nanoparticles (A). The film strongly absorbs visible light over a large wavelength range and appears completely dark. FIG. 3 also shows an SEM image (B) collected on the surface of a composite with 8% nanoparticles, where nanoparticles dispersed homogeneously on the surface are visible at high magnification. EDX result, as shown in FIG. 3, demonstrates signals of bismuth element against background silicon (B, inset). The Young's modulus of the composite decreases with increase in the nanoparticle loading (C), meaning that introduction of bismuth nanoparticles leads to more defects in the polymer and weakens its strength, but the composite is sufficiently elastic at 4% by mass of nanoparticles. In contrast, the composite formed by polymer and bismuth microparticles is much weaker (Young's modulus of $5\times10^4$ kPa) compared to that formed by nanoparticles of the mass same ratio. In light of recent discovery that cellulose can provide highest mechanical strength compared to its weight, it is possible that polymer fibers with incorporated bismuth nanoparticles could be woven into fabrics. Gas permeability of nanoparticle-polymer composite was examined with water retention experiment where the composite was immersed into water and the mass of the composite was measured over time. FIG. 3 also shows the mass of a composite increases to 1.3 times of its initial mass in 5 days (D). The porosity of the composite is then estimated to be about 35.4% given the density of the composite of 1,180 kg/m$^3$.

Figure 4:
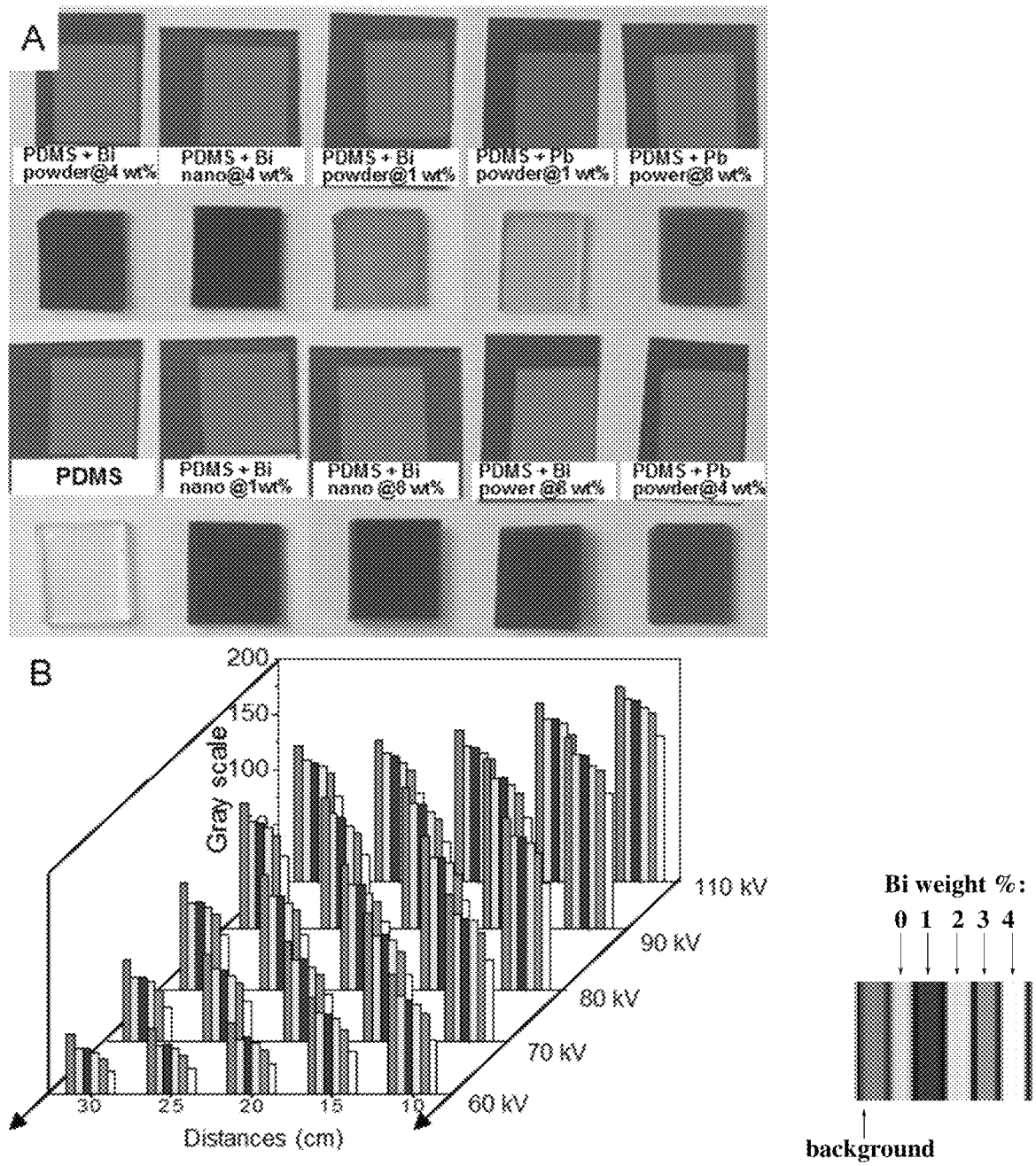
FIG. 4 shows digital images of polymer composites that contain different amounts of particles (micro and nano), and different materials (bismuth and lead), as well as exposed GafChromic™ films (A); X-ray energy and flux (distance from X-ray tube) dependent attenuation efficiency of polymer composites with different loading of bismuth nanoparticles (B).

The X-ray attenuation ability of bismuth nanoparticle-polymer composite was assessed by exposing composite films (thickness of 5 mm) to a cone shaped X-ray beam, and allowing transmitted X-ray expose an underlying GafChromic™ film. FIG. 4 shows the optical images of composite films and X-ray exposed GafChromic™ films (A), where more transparent composite film contains less nanoparticles, and causes more exposure in GafChromic™ film (darker). The optical density of exposed GafChromic™ films recorded with densitometer was used to determine the intensity of transmitted X-ray beam (B), where the transmitted dose of 60 kV X-ray beam decreases from 0.941 to 0.032 Gy as the mass ratio of bismuth nanoparticles in composite film increases from 0 to 4%. The attenuation ratio of bismuth nanoparticles reaches 96.6 at 8.0% by mass compared to polymer film of the same thickness. At higher X-ray energy, all composite samples become less effective at attenuating higher energy photons, and more X-ray photons pass through the composite film to expose GafChromic™ film. The stabilities of nanoparticle-polymer composites against 60 kV X-ray exposure were measured and no degradation has been observed over 2.5 h period. The stabilities of bismuth nanoparticle-polymer composite in HCl (0.1 M) and NaOH (2 N) solutions were examined after immersing composites in respective solutions for two weeks. No significant change in attenuation ability was found before and after immersion, meaning that the nanoparticles are protected by the surrounding polymer matrix and thus immune to acid and base conditions.

Figure 5:
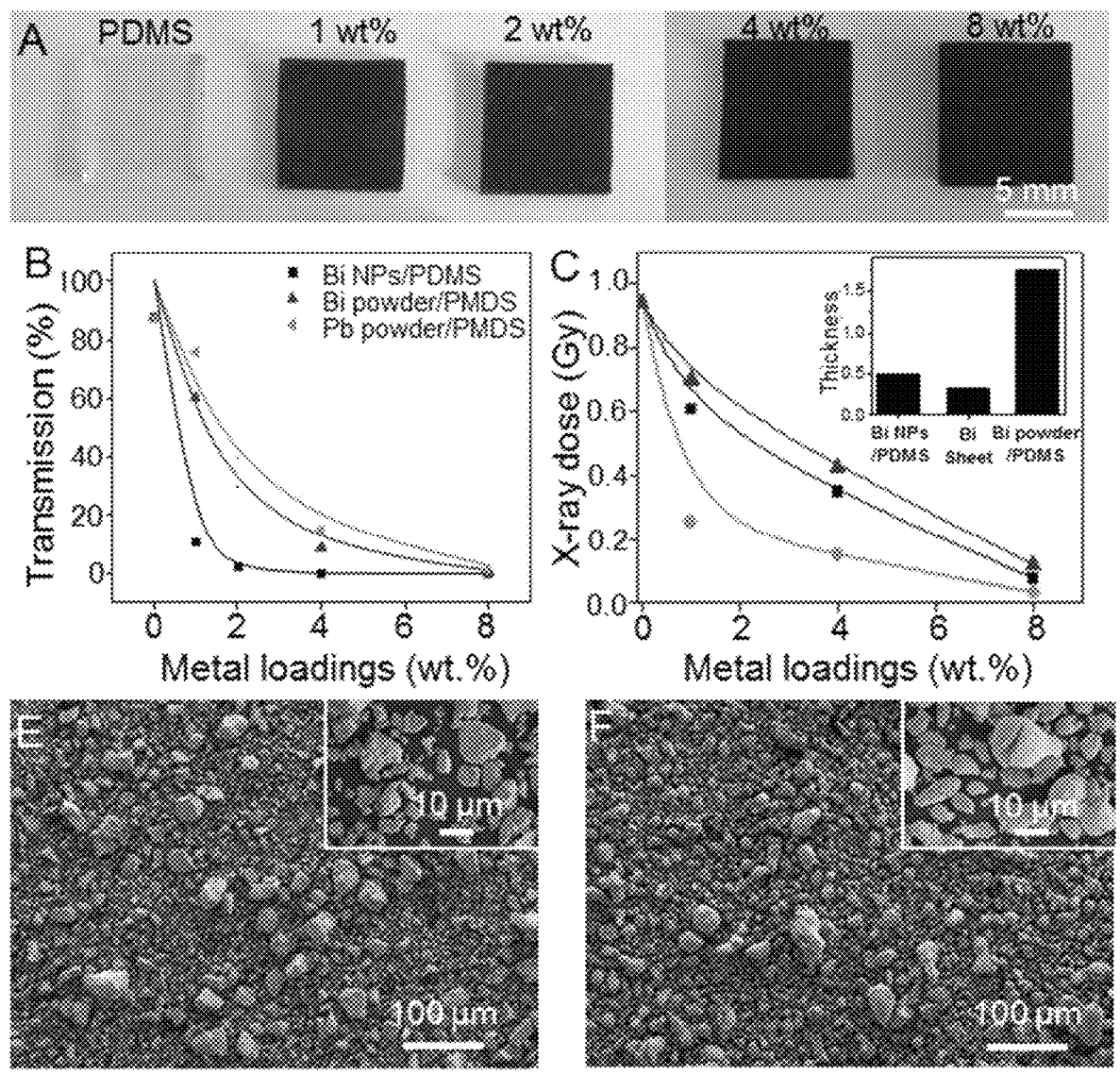
FIG. 5 shows digital images of polymer and its composites (1 cm×1 cm×0.5 cm) with different amount of bismuth nanoparticles (A); wavelength dependent light transmissions (B) of polymer composites with different amount of bismuth nanoparticles, bismuth microparticles, and lead microparticles; the attenuations of 60 kV X-ray (C) by polymer composites with different amount of bismuth nanoparticles (squares), bismuth microparticles (triangles), and lead microparticles (circles); SEM images of bismuth microparticles (E) and lead microparticles (F).

Both X-ray and optical transmissions of the nanoparticle-polymer composites have been determined. FIG. 5 shows the optical graphs of five composite films containing 0, 1.0, 2.0, 4.0 and 8.0% of bismuth nanoparticles (A), where the film color changes from transparent to dark when the mass ratio of nanoparticles increases. FIG. 5 also shows the light transmissions of 5 mm thick polymer composites containing different amount of bismuth nanoparticle, bismuth microparticles and lead microparticles (B). FIG. 5 additionally shows the relative intensities of 60 kV X-ray transmitted through the polymer films that contain bismuth nanoparticles, bismuth microparticles and lead microparticles (C). Both plots show the same trend of change in transmission as the amount of particles increases. Both plots show a significant reduction in transmission (large slope) when the mass ratio of nanoparticles is below 2%; after that, the slope is small and there is only small reduction in transmission. FIG. 5 also shows micrographs of polymer composites of bismuth microparticles (E) and lead microparticles (F) with diameter of 5 μm have been made and examined, where the X-ray (and optical) transmissions and the mass ratios of microparticles show similar trend, and the slopes are smaller than those of nanoparticle composites. The nearly identical trends observed in optical and radiation transmissions of particle-polymer composites suggest a common basis for nanoparticle-enhanced radiation shielding and visible light blocking.

Cellulous nanofibers facilitate even distribution of bismuth nanoparticles in polymer, which allows a minimal amount of bismuth material to cover the whole area exposed to light or X-ray beam. Given the low attenuation ability of polymer, the shielding abilities of the composites can be derived by considering particle size and their packing in the direction normal to incoming X-ray. The intensity (I) of X-ray (or light) after passing through a length of d cm in a diluted solution with n particles per unit volume can be determined as follows:

$$\frac{I}{I_0} = \exp(-nCd) \quad (2)$$

where h is the intensity of incoming X-ray or light, and C is the extinction coefficient (cross section) at certain energy (wavelength) of single particle that depends on the material property and particle geometry. The mass balance of particles in the particle-polymer composite can be established as $$N\rho 4/3\pi r^3 = x\rho_m V_{comp} \quad (3)$$

where N is the total number of particles in the composite with volume $V_{comp}$, r is the radius of particle, x is the mass ratio of the particles in the composite, $\rho$, $\rho_m$ are the densities of particle and polymer, respectively. Given the low mass ratio of particles, the density of the composite can be taken as that of the polymer. Therefore, the number of particles per unit volume can be derived as:

$$n = \frac{N}{V} = \frac{3x\rho_m}{4\rho\pi r^3} \quad (4)$$

The intensity of transmitted X-ray (or light) can be determined by combining equations (2) and (4) using $$\frac{I}{I_0} = \exp(-kx), \text{ where } k = \frac{3\rho_m c d}{4\rho\pi r^3} \quad (5)$$

The X-ray (or light) attenuation ability of the composites can be assessed with k values, which can be derived by fitting optical (B) and X-ray (C) transmission data, as shown in FIG. 5, to equation (4). It is found that bismuth nanoparticles have a k value of 91.68 (black), which is approximately four times higher than those of bismuth powder (26.27) and lead powder (19.67). The good agreement between the simulation and transmission results suggests the equation can be used to predict the shielding ability of any materials. The X-ray shielding ability of the nanoparticle-polymer composite was compared to those of microparticle-polymer composite and bismuth sheet at the mass attenuation coefficient (μ/ρ) of 5.74 cm²/g for 60 keV monoenergetic X-ray using Lambert-Beer law $$\frac{I}{I_0} = \exp\left(-\frac{\mu}{\rho}d\right) \quad (6)$$

As shown in FIG. 5, it was found the shielding ability of a 0.5 cm thick polymer containing 2% (mass) of 5 nm nanoparticles is equivalent to that of 0.32 cm thick bismuth sheet, and also equivalent to 1.75 cm thick polymer containing 2% (mass) of 5 μm bismuth power, (C, inset). If the 0.5 cm 2% nanoparticle-polymer composite is used in abdomen computed tomography scanning, it can reduce dose received by human body from 8 to less than 0.017 mSv, which is equivalent to the reduction of background radiation from 2.7 years to less than 1 month.

The enhanced radiation shielding with the nanoparticle composites can be attributed to the size effect. Given the same mass ratio of nanoparticles in composites, the number of individual particles is larger in the case of nanoparticles compared to microparticles, the voids between nanoparticles are smaller, and the nanoparticle multi-layers are stacked together to block X-ray beams. In addition, multiple scattering of X-ray photon increases as the number of particles increases, which increases the optical pathway of X-ray photons and leads to high absorption. In the case of larger particles, voids between particles are larger and less multiple scattering of X-ray occurs due to smaller number of particles. In order to achieve the same shielding effect, more particles will have to be used to cover inter-particle spaces and cause more scattering, which could cause mass increase of the composite. In principle, making even smaller nanoparticles or metal atoms will enhance the shielding effect further, however, metal atoms in polymer may leak due to high diffusion ability. The nanoparticles of the present disclosure are sufficiently large that the diffusion into the aqueous solution is minimized.

In some embodiments, the invention relates to ultra-small bismuth nanoparticles made with cellulose nanofibers added into a polymer. The cellulose nanofibers form an interpenetrating network with polymer chains and ensure homogeneous dispersion of bismuth nanoparticles. The radiation attenuation ability of the composite was assessed in transmission mode, and compared to that of microparticle composites. It was found that the nanoparticles can effectively shield X-ray radiation at lower mass ratio in polymer matrix. The enhanced radiation shielding is attributed to close packing of nanoparticles normal to incoming X-ray direction, which is enabled by strong affinity of the nanoparticles to the interstitial space of nanofibers and uniform distribution of the nanoparticles in polymer.

Exemplary Features of the Technology

Effective radiation shielding achieved with light-weight polymer-nanoparticle composite Simple preparation of nanoparticles with nanocellulose matrix Even distribution of nanoparticles within polymer Dense packing of nanoparticles with minimum void space Flexibility, workability, chemical stability, and low cost of polymer-nanoparticle composite Exemplary Advantages and Improvements Over Existing Methods, Devices, or Materials Existing polymer composites with microparticles (powders) contain larger voids, and thus require more powders to achieve sufficient shielding, which makes protection equipment heavier and more expensive.

Ultra-small bismuth nanoparticles can be packed densely in polymer to minimize void space.

Existing polymer composites with microparticles (powders) are mechanically weaker, and the metal powders may leak.

Polymer composites with nanoparticles are tougher, and can last longer than existing microparticle-based ones.

Light-weight and low-cost radiation and electromagnetic shielding equipment (apron, vest, outfit).

Exemplary Commercial Applications

Light and low-cost radiation and electromagnetic wave attenuated apron for pregnant women X-ray protection shield used healthcare employees for diagnostic X-ray examinations Radiation protection for workers in heavy metal manufacturing companies X-ray shield outfits or masks for communities working in ground nuclear weapons testing Cosmic ray protection for pilots or astronauts in aerospace research As used herein, "nanocellulose" refers to one or more of cellulose nanofibers, bacterial nanocellulose, or cellulose nanocrystals, which may generally, on average, have a width of from about 3 to about 50 nm (cellulose nanofibers), about 20 to about 100 nm (bacterial nanocellulose) or about 3 to about 20 nm (cellulose nanocrystals) and a length of about 0.1 to about 5 micrometers (μm) (cellulose nanofibers), about 1 to about 5 μm (bacterial nanocellulose) or about 50 to about 100 nm (cellulose nanocrystals). Examples of production and use of cellulose nanofibers, bacterial nanocellulose, and/or cellulose nanocrystals are described in U.S. Pat. Nos. 8,9746,34, 8,900,706, and 8,710,213, and U.S. Patent Application Publication Nos. 2017/0283764 and 2015/0225486, each of which is incorporated herein by reference in its entirety.

As used herein, "electromagnetic radiation" refers to radio waves, microwaves, infrared light, visible light, ultraviolet light, X-rays, and gamma rays. For example, electromagnetic radiation can refer to ionizing radiation, such as high frequency ultraviolet radiation, X-rays and gamma rays. The term "X-rays" refers to photons with energies in the range from about 100 eV to about 200 keV.

As used herein, "surface-modifying agent" refers to an organic or inorganic molecule or a polymer that can covalently or non-covalently attach to the surface of the metal nanoparticle and modify the surface of the nanoparticle in a way that increases the interaction between the surface of the nanoparticle and the polymer matrix. The improved interaction of the nanoparticles with the polymer matrix increases dispersion of the nanoparticles in the polymer and decreases aggregation of the nanoparticles. Examples of surface-modifying agents are described, for example, in U.S. Pat. Nos. 7,629,027, and 9,650,536, and U.S. Patent Application Publication No. 2006/0083694, each of which is incorporated herein by reference in its entirety.

In some embodiments, the present disclosure relates to a composite material, comprising a polymer, a plurality of metal nanoparticles, and a surface-modifyng agent. In certain embodiments, the surface-modifying agent is nanocellulose.

In certain embodiments, the polymer is selected from the group consisting of polydimethylsiloxane (PDMS), cellulose, polyamide, polyacrylonitrile, polypropylene, polyvinyl chloride, epoxy resin, polyimide, polyurethane, polyurethane polyvinylidene fluoride, and polyvinyledene difluoride.

In some embodiments, the polymer is PDMS.

In some embodiment, the plurality of metal nanoparticles comprises nanoparticles, wherein each of the nanoparticles comprises:

one or more elements with atomic numbers 20-118, oxides of one or more elements with atomic numbers 20-118, or sulfates of one or more elements with atomic numbers 20-118.

In certain embodiments, the plurality of metal nanoparticle comprises metal nanoparticles selected from the group consisting of lead nanoparticles, tungsten nanoparticles, bismuth nanoparticles, and uranium nanoparticles. For example, the plurality of metal nanoparticle comprises bismuth nanoparticles.

In some embodiments, the average size of the metal nanoparticles is from about 1 nm to about 40,000 nm, or from about 1 nm to about 40 nm, or from about 1 nm to about 20 nm. For example, the average size of metal nanoparticles may be about 5 nm.

In some embodiments, the amount of the metal nanoparticles in the composite material is from 0.5 wt. % to about 40 wt. %. For example, the amount of the metal nanoparticles in the composite is about 2 wt. %.

In some embodiments, nanocellulose comprises cellulose nanofibers.

In some embodiments, nanocellulose comprises cellulose nanocrystals. In certain embodiments, the amount of nanocellulose in the composite material is from 0.5 wt. % to about 40 wt. %.

In some embodiments, the present disclosure relates to a film comprising one or more composite materials.

In certain embodiments, the thickness of the film is from about 100 nm to about 10 cm. For example, the thickness of the film is about 0.5 cm.

In some embodiments, the present disclosure relates to a method for shielding a subject from electromagnetic radiation, comprising placing one or more composite materials between the subject and a source of electromagnetic radiation, thereby reducing a dose of electromagnetic radiation received by the subject.

In certain embodiments, the dose of electromagnetic radiation received by the subject is reduced by amount from 90% to 100%, such as by 90%, by 91%, by 92%, by 93%, by 94%, by 95%, by 96%, by 97%, by 99%, or by 100%. For example, the dose of electromagnetic radiation received by the subject is reduced by amount from 95% to 99%. In some embodiments the dose of electromagnetic radiation received by the subject is reduced by 96%.

In some embodiments, electromagnetic radiation is X-ray radiation.

Materials and Methods

The following chemicals were obtained from Aldrich and used without purification: tetramethyl-1-piperidinyloxy (TEMPO), bismuth nitrate ($(Bi(NO_3)_3 \cdot 5H_2O)$), sodium borohydride ($NaBH_4$), sodium hypochlorite (NaClO), sodium bromide (NaBr), dimethyl sulfoxide (DMSO). and hydrogen chloride (HCl). Polydimethylsiloxane (Slygard 184 PDMS) was obtained from Dow Chemical, and Celgar kraft bleached softwood pulp was obtained from VWR.

EXAMPLE 1

Preparation of Bi-Nanoparticle Polymer Composite Films

Cellulose nanofibers were prepared from softwood pulp with TEMPO oxidation method: 5 g of cellulose fibers, 78 mg of TEMPO, and 514 mg of NaBr were mixed in 100 mL water and added to a NaClO solution (5%) where pH was adjusted to 10 by addition of diluted HCl. After 10 hours the cellulose nanofibers were centrifuged, purified by dialysis until eluate was neutralized, and dispersed in water under ultrasonication. Bismuth nanoparticles were made as follows: 0.0485 g of $Bi(NO_3)_3 \cdot 5H_2O$ was dissolved in 10 mL deionized (DI) water under nitrogen atmosphere, followed by addition of 1 mL suspension of 2.0% (by mass) cellulose nanofibers with stirring for 10 minutes. Addition of 700 µL of 1 M $NaBH_4$ aqueous solution to the above mixture caused nanoparticle formation. The nanoparticle suspension was centrifuged with de-ionized (DI) water. After removing the supernatant, the nanoparticles were frozen at −20° C., and placed under vacuum (0.133 mBar at −50° C.) for 24 hours to complete lyophilization. Polymer composite film was made by adding lyophilized nanoparticles into a mixture of PDMS prepolymer (10 parts) and curing agent (1 part), agitating the mixture and removing bubbles, casting the mixture in a petri dish to form a film, and heating the obtained film at 60° C. for 5 hours to complete polymerization. The polymer composite films with bismuth and lead microparticles were also prepared for comparison. Microparticles were dispersed in a mixture of PDMS prepolymer and curing agent, the mixture was agitated, casted to form a film, and heated at 60° C. for 5 hours to complete polymerization and obtain the film.

Nanoparticles were imaged with a high-resolution transmission electron microscope (JEOL 1010, TEM) operated at an accelerating voltage of 100 kV. An aqueous suspension of nanoparticles was dropped on carbon coated copper grids and dried at room temperature. The microparticles and the cross sections of polymer composites were imaged with a Zeiss scanning electronic microscope (Ultra 55 SEM) operated at an accelerating voltage of 5 kV in secondary electron mode. A Faxitron X-ray machine with copper target was operated in the voltage range of 60 to 100 kV and 10 mA to generate monenergistic X-ray. The X-ray dose rate was determined with reflective-type XR-RV3 GafChromic™ films (a radiation sensitive dosimetry film, International Specialty Products, Wayne) that are sensitive in the 0.05 to 15 Gy range within energy range of 30 keV to 30 MeV. The optical density of exposed GafChromic™ films was recorded with a transmission densitometer (Tobias TBX1000/1500). The X-ray shielding abilities of PDMS films with different particles (bismuth and lead) and different composition (0, 1, 2, 3, and 4 wt %) were evaluated by GafChromic™ films under different voltage. The distance between outlet of X-ray tube and sample was adjusted to control the flux (dose) of X-ray. The tensile strength of composite film was measured on a test instrument (Electro Force 3200 TA Instruments) at 0.08 mm/s tensile velocity. A PerkinElmer differential scanning calorimetry (DSC7) was used to determine the melting temperature of bismuth nanoparticles and microparticles. An atomic force microscope (Dimension Edge, Bruker) was used to image cellulose nanofibers in tapping mode at scan rate of 1 Hz. An Ultima IV X-ray diffractometer (Rigaku, Japan) with Cu Kα radiation was used to obtain X-ray diffraction (XRD) patterns of nanoparticles.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES CITED

1. Curtis, H. J., Limitations on Space Flight Due to Cosmic Radiations. *Science* 1961, 133, 312-316.
2. Gupta, T. K.; Singh, B. P.; Singh, V. N.; Teotia, S.; Singh, A. P.; Elizabeth, I.; Dhakate, S. R.; Dhawan, S. K.; Mathur, R. B., Mno2 Decorated Graphene Nanoribbons with Superior Permittivity and Excellent Microwave Shielding Properties. *Journal of Materials Chemistry A* 2014, 2, 4256-4263.
3. Hull, A. P., Rediation Protection. *Science* 1971, 174, 1280-1281.
4. Martinez, L. M.; Kingston, J., Space Radiation Analysis: Radiation Effects and Particle Interaction Outside the Earth's Magnetosphere Using Gras and Geant4. *Acta Astronautica* 2012, 72, 156-164.
5. Kim, S. C.; Choi, J. R.; Jeon, B. K., Physical Analysis of the Shielding Capacity for a Lightweight Apron Designed for Shielding Low Intensity Scattering X-Rays. *Scientific Reports* 2016, 6, 27721.
6. Roof, R. B., X-Ray Absorption Coefficients of Thorium, Uranium, and Plutonium-Experimental Determination and Theoretical Interpretation. *Physical Review* 1959, 113, 820-825.

7. Kazempour, M.; Saeedimoghadam, M.; Shekoohi Shooli, F.; Shokrpour, N., Assessment of the Radiation Attenuation Properties of Several Lead Free Composites by Monte Carlo Simulation. *Journal of Biomedical Physics & Engineering* 2015, 5, 67-76.
8. Hyun, S.; Kim, K.; Jahng, T.; Kim, H., Efficiency of Lead Aprons in Blocking Radiation—How Protective Are They? *Heliyon* 2016, 2, 1-14.
9. Ambika, M. R.; Nagaiah, N.; Suman, S. K., Role of Bismuth Oxide as a Reinforcer on Gamma Shielding Ability of Unsaturated Polyester Based Polymer Composites. *Journal of Applied Polymer Science* 2016, 134, 1-7.
10. Badawy Sayed, M.; Abd El-Latif, A. A., Synthesis and Characterizations of Magnetite Nanocomposite Films for Radiation Shielding. *Polymer Composites* 2015, 38, 974-980.
11. Christodoulou, E. G.; Goodsitt, M. M.; Larson, S. C.; Darner, K. L.; Satti, J.; Chan, H., Evaluation of the Transmitted Exposure through Lead Equivalent Aprons Used in a Radiology Department, Including the Contribution from Backscatter. *Medical Physics* 2003, 30, 1033-1038.
12. Kandanapitiye, M. S.; Gao, M.; Molter, J.; Flask, C. A.; Huang, S. D., Synthesis, Characterization, and X-Ray Attenuation Properties of Ultrasmall Bioi Nanoparticles: Toward Renal Clearable Particulate Ct Contrast Agents. *Inorganic Chemistry* 2014, 53, 10189-10194.
13. Liu, J.; Zhang, Q.; Sun, N.; Zhao, Y.; Shi, R.; Zhou, Y.; Zheng, J., Elevated Gamma-Rays Shielding Property in Lead-Free Bismuth Tungstate by Nanofabricating Structures. Journal of *Physics and Chemistry of Solids* 2018, 112, 185-189.
14. Tishkevich, D. I.; Grabchikov, S.; Lastovskii, S.; Trukhanov, S.; Zubar, T.; Vasin, D.; Trukhanov, A. V., Effect of the Synthesis Conditions and Microstructure for Highly Effective Electron Shields Production Based on Bi Coatings. *ACS Applied Energy Materials* 2018, 1, 1695-1702.
15. Wu, Y.; Zhang, Q.; Zhou, D.; Liu, L.; Xu, Y.; Xu, D.; Zhou, Y., One-Dimensional Lead Borate Nanowhiskers for the Joint Shielding of Neutron and Gamma Radiation: Controlled Synthesis, Microstructure, and Performance Evaluation. CrystEngComm 2017, 19, 7260-7269.
16. Zhou, D.; Zhang, Q.; Zheng, J.; Wu, Y.; Zhao, Y.; Zhou, Y., Co-Shielding of Neutron and r-Ray with Bismuth Borate Nanoparticles Fabricated Via a Facile Sol-Gel Method. Inorganic Chemistry Communications 2017, 77, 55-58.
17. J. Yaffe, M.; E. Mawdsley, G.; Lilley, M.; Servant, R.; Reh, G., Composite Materials for X-Ray Protection. *Health physics* 1991, 60, 661-664.
18. McCaffrey, J. P.; Shen, H.; Downton, B.; Mainegra—Hing, E., Radiation Attenuation by Lead and Nonlead Materials Used in Radiation Shielding Garments. *Medical Physics* 2007, 34, 530-537.
19. Mesbahi, A.; Ghiasi, H., Shielding Properties of the Ordinary Concrete Loaded with Micro- and Nano-Particles against Neutron and Gamma Radiations. *Applied Radiation and Isotopes* 2018, 136, 27-31.
20. Li, R.; Gu, Y.; Wang, Y.; Yang, Z.; Li, M.; Zhang, Z., Effect of Particle Size on Gamma Radiation Shielding Property of Gadolinium Oxide Dispersed Epoxy Resin Matrix Composite. *Materials Research Express* 2017, 4, 035035-035045.
21. Guo, R.; Wang, H.; Peng, C.; Shen, M.; Pan, M.; Cao, X.; Zhang, G.; Shi, X., X-Ray Attenuation Property of Dendrimer-Entrapped Gold Nanoparticles. *The Journal of Physical Chemistry C* 2010, 114, 50-56.
22. Nambiar, S.; Yeow, J. T. W., Polymer-Composite Materials for Radiation Protection. *ACS Applied Materials & Interfaces* 2012, 4, 5717-5726.
23. Kim, H. J.; Lee, K. J.; Seo, Y.; Kwak, S.; Koh, S. K., Hdpe Surface Functionalization by Low-Energy Ion-Beam Irradiation under a Reactive O2 Environment and Its Effect on the Hdpe/Nylon 66 Blend. *Macromolecules* 2001, 34, 2546-2558.
24. Kim, Y.; Park, S.; Seo, Y., Enhanced X-Ray Shielding Ability of Polymer—Nonleaded Metal Composites by Multilayer Structuring. *Industrial & Engineering Chemistry Research* 2015, 54, 5968-5973.
25. Li, R.; Gu, Y.; Yang, Z.; Li, M.; Hou, Y.; Zhang, Z., Gamma Ray Shielding Property, Shielding Mechanism and Predicting Model of Continuous Basalt Fiber Reinforced Polymer Matrix Composite Containing Functional Filler. *Materials & Design* 2017, 124, 121-130.
26. Li, Z.; Nambiar, S.; Zheng, W.; Yeow, J. T. W., Pdms/Single-Walled Carbon Nanotube Composite for Proton Radiation Shielding in Space Applications. *Materials Letters* 2013, 108, 79-83.
27. Li, Z.; Chen, S.; Nambiar, S.; Sun, Y.; Zhang, Q.; Zheng, W.; Yeow, J. T. W., Pmma/Mwcnt Nanocomposite for Proton Radiation Shielding Applications. *Nanotechnology* 2016, 27, 234001-234010.
28. Reichmanis, E.; Frank, C. W.; O'Donnell, J. H.; Hill, D. J. T., Radiation Effects on Polymeric Materials. *Irradiation of Polymeric Materials* 1993, 527, 1-8.
29. Nambiar, S.; Osei, E. K.; Yeow, J. T. W.; Osei, E. K., Effects of Particle Size on X-Ray Transmission Characteristics of Pdms/Ag Nano- and Microcomposites. 2015 *IEEE 15th International Conference on Nanotechnology (IEEE-NANO)* 2015, 1358-1361.
30. Slaba, T. C.; Bahadori, A. A.; Reddell, B. D.; Singleterry, R. C.; Clowdsley, M. S.; Blattnig, S. R., Optimal Shielding Thickness for Galactic Cosmic Ray Environments. *Life Sciences in Space Research* 2017, 12, 1-15.
31. Zhang, X.; Yang, M.; Zhang, X.; Wu, H.; Guo, S.; Wang, Y., Enhancing the Neutron Shielding Ability of Polyethylene Composites with an Alternating Multi-Layered Structure. *Composites Science and Technology* 2017, 150, 16-23.
32. Soylu, H. M.; Yurt Lambrecht, F.; Ersöz, O. A., Gamma Radiation Shielding Efficiency of a New Lead-Free Composite Material. Journal of Radioanalytical and Nuclear Chemistry 2015, 305, 529-534.
33. Viegas, J.; Silva, L. A.; Batista, A. M. S.; Furtado, C. A.; Nascimento, J. P.; Faria, L. O, Increased X-Ray Attenuation Efficiency of Graphene-Based Nanocomposite. *Industrial & Engineering Chemistry Research* 2017, 56, 11782-11790.

What is claimed is:
1. A composite material, comprising a polymer, a plurality of metal nanoparticles, and a surface-modifying agent, wherein:
   the polymer is selected from the group consisting of polydimethylsiloxane (PDMS), polyamide, polyacrylonitrile, polyethylene, polypropylene, polyvinyl chloride, epoxy resin, polyimide, polyurethane, polyurethane polyvinylidene fluoride, and polyvinylidene difluoride;
   the surface-modifying agent is nanocellulose;
   the surface-modifying agent and the polymer form an interpenetrating network; and the plurality of metal nanoparticles comprises metal nanoparticles selected from the group consisting of lead nanoparticles, tungsten nanoparticles, bismuth nanoparticles, and uranium nanoparticles.

2. The composite material of claim 1, wherein the polymer is PDMS.

3. The composite material of claim 1, wherein the plurality of metal nanoparticles comprises bismuth nanoparticles.

4. The composite material of claim 1, wherein the average size of the plurality of metal nanoparticles is from 1 nm to 40,000 nm.

5. The composite material of claim 1, wherein the average size of the plurality of metal nanoparticles is 5 nm.

6. The composite material of claim 1, wherein the amount of the plurality of metal nanoparticles in the composite material is from 0.5 wt. % to 40 wt. %.

7. The composite material of claim 1, wherein the amount of the plurality of metal nanoparticles in the composite is 2 wt. %.

8. The composite material of claim 1, wherein nanocellulose comprises cellulose nanofibers.

9. The composite material of claim 1, wherein nanocellulose comprises cellulose nanocrystals.

10. The composite material of claim 1, wherein the amount of nanocellulose in the composite material is from 0.5 wt. % to 40 wt. %.

11. A film comprising at least one composite material of claim 1.

12. A method for shielding a subject from electromagnetic radiation, comprising placing at least one composite material of claim 1 between the subject and a source of electromagnetic radiation, thereby reducing a dose of electromagnetic radiation received by the subject.

13. The method of claim 12, wherein the dose of electromagnetic radiation received by the subject is reduced by an amount from 95% to 99%.

14. The method of claim 12, wherein the dose of electromagnetic radiation received by the subject is reduced by at least 96%.

15. The method of claim 12, wherein the electromagnetic radiation is X-ray radiation.

* * * * *